US00PP10246P

United States Patent [19]

Cornelis

[11] Patent Number: Plant 10,246

[45] Date of Patent: Feb. 17, 1998

[54] SPATHIPHYLLUM PLANT NAMED 'FREDERICK'

[75] Inventor: Daniel Cornelis, Melsen, Belgium

[73] Assignee: Reginald Deroose, Evergem, Belgium

[21] Appl. No.: 622,394

[22] Filed: Mar. 27, 1996

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 8,655 3/1994 Cornelis ..... Plt./88.1
P.P. 8,839 7/1994 DeCoster ..... Plt./88.1
P.P. 8,844 7/1994 van Dordrecht ..... Plt./88.1
P.P. 8,849 7/1994 Caldwell ..... Plt./88.1

OTHER PUBLICATIONS

VPOVROM—Plant Variety Database 1996/03, Dec. 23, 1996, "Frederick".

*Primary Examiner*—Howard J. Locker
*Attorney, Agent, or Firm*—Foley & Lardner

[57] ABSTRACT

A new and distinct spathiphyllum plant named 'Frederick', characterized by its medium growth habit, relatively large recumbent leaves, large white spathes relative to size and shape of plant, short strong flower stems, and its very rich flowering.

1 Drawing Sheet

The present invention comprises a new and distinct cultivar of spathiphyllum, botanically known as Spathiphyllum hybrid, and hereinafter referred to by the cultivar name 'Frederick'.

The breeding program eventually resulting in the new cultivar was originated approximately twenty years ago by the inventor Daniel Cornelis in Melle, Belgium. The initial crosses were between the well-known spathiphyllum hybrid cultivar 'Mona Loa' and an unnamed cultivar of *Spathiphyllum walissii*. A large number of seedlings were selected from the original cross and the best of these were again used for crossing in a continuation of the breeding program. The first and subsequent generations of seedlings used for breeding purposes are not specifically identifiable at this time.

The new cultivar 'Frederick' was produced from a subsequent cross of presently unknown parents made by Daniel Cornelis in 1988 in Melle, Belgium. 'Frederick' was discovered and selected as a flowering plant within the progeny of the cross in July 1988 by Daniel Cornelis in Melle, Belgium.

Subsequent asexual reproduction by tissue culture, first performed in September 1992 in Evergem, Belgium under the supervision of the inventor, has demonstrated that the combination of characteristics as herein disclosed for the new cultivar are firmly fixed and are retained through successive generations of asexual reproduction.

The following traits have been repeatedly observed and in combination distinguish 'Frederick' as a new and distinct cultivar:

1. 'Frederick' is a medium size spathiphyllum with rather large leaves and impressed veins.
2. 'Frederick' has large flowers in comparison with the shape of the plant. The term "flower" refers throughout the specification to the inflorescence including the spathe and the spadix.
3. The plant has a strong short flower stem.
4. The leaf margin is slightly waved.
5. The leaves bend down particularly at the tips.
6. Abundant flowering, with several white flowers normally in bloom at the same time.

The following observations, measurements and values describe plants grown in Melle, Belgium under greenhouse conditions which closely approximate those generally used in horticultural practice. Color references are made to The Royal Horticultural Society (R.H.S.) Color Chart, except where general color terms of ordinary significance are used. The color values were determined between 10 AM and Noon in July 1992 under slightly clouded but bright daylight conditions at Melle, Belgium.

The accompanying color photograph shows in front view the unique features of the new cultivar. The colors are as accurate as possible with color illustrations of this type.

The new cultivar can be compared to the spathiphyllum cultivar 'Snow White', disclosed in U.S. Plant Pat. No. 7,712. The cultivars are similar with respect to plant size, flower shape, white spathe color, and leaf color. 'Frederick' differs from 'Snow White' in that 'Frederick' has wider and recumbent leaves, a wider or more spreading plant habit, larger flowers, a storage fragrance, and greater floriferousness, with several flowers blossoming at the same time.

Classification: Spathiphyllum hybrid cv. Frederick.

Parentage: Male and female parents unknown. The parents are generational descendants of an original cross between Spathiphyllum 'Mona Loa' and an unnamed cultivar of *Spathiphyllum walissii*.

Propagation: Vegetatively propagated by tissue culture.

Plant: A mature plant is 50 to 60 cm tall, inclusive of flowers, when grown in a 13 cm pot measured from the soil line and approximately 45 to 55 cm in diameter. Without flowers, the plant is approximately 30 to 40 cm in height.

Leaves:

*Form and size.*—Elliptic, nearly symmetrical. Length: 25 to 30 cm. Width: 10 to 15 cm.

*Texture.*—Leathery, upper surface glossy.

*Veins.*—Medium bulging between veins.

*Color*—Upper surface: 137 A, but slightly darker. Lower surface: 137 C.

*Leaf petiole.*—Length: 13 to 23 cm. Width: 0.5 to 0.7 cm.

*Petiole wings.*—Widest width: 1 cm. Distance between top of the wings and base of the leaf: 2.5 to 3.5 cm.

Inflorescence:

*Buds.*—Formed in axils of leaves.

Spathe:

*Size.*—Length: 21 to 24 cm Width: 10 to 12 cm

*Location to the flower stem.*—Generally parallel

*Shape.*—Oval, slightly asymmetrical

*Flowering time.*—Flowers repeatedly. First flower appears after 7 months. The flowers last for one month.

*Flower stem.*—Length: 20 to 25 cm starting from the sheath of the leaf. Width: 0.6 cm Total length of the flower and the flower stem: 40 to 50 cm. Angle of the flower stem relative to the leaf base: 30° to 40°.

*Color.*—White, 155D.

*Fragrance.*—Relatively strong and pleasant.

Spadix:

*Size.*—7 to 8 cm in length.

*Longevity.*—4 weeks.

*Position of the spathe relative to the spadix.*—At approximately midway of the length of the spadix, it is spaced 1 cm from spathe and generally parallel to the spathe at the midpoint of the spathe.

*Color.*—White, 158A.

Reproductive organs:

*Stamens.*—White.

*Anthers and filaments.*—White.

*Pollen.*—White.

*Pistils.*—White.

Roots: White, fleshy roots with fine laterals.

Disease resistance: In cultivation to date, 'Frederick' has not shown susceptibility to disease.

I claim:

1. A new and distinct cultivar of spathiphyllum plant named 'Frederick' as illustrated and described.

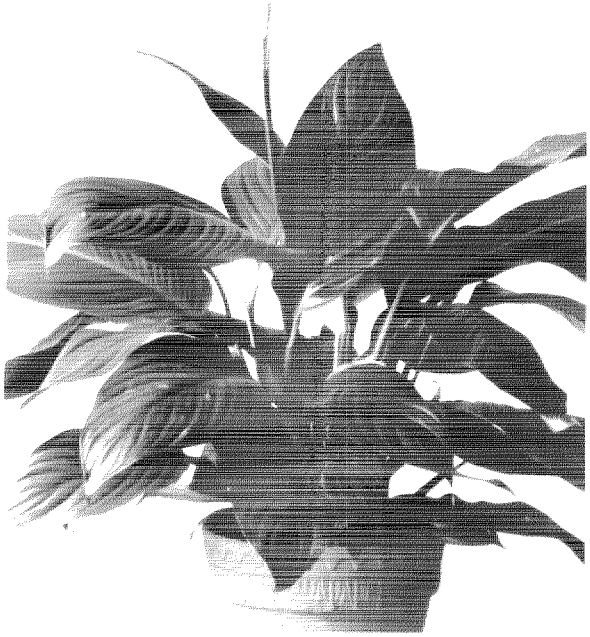

* * * * *